United States Patent [19]

Shah

[11] Patent Number: 5,370,878
[45] Date of Patent: Dec. 6, 1994

[54] METHOD FOR PREPARING A DIRECT COMPRESSION GRANULATED ACETAMINOPHEN COMPOSITION

[75] Inventor: Kamlesh B. Shah, Dayton, N.J.

[73] Assignee: Hallmark Pharmaceuticals, Inc., Somerset, N.J.

[21] Appl. No.: 129,325

[22] Filed: Sep. 30, 1993

[51] Int. Cl.⁵ .................... A61K 31/05; A61K 9/26; A61K 47/38
[52] U.S. Cl. ................... 424/469; 424/465; 424/470; 424/486
[58] Field of Search .............. 424/469, 470, 486

[56] References Cited

U.S. PATENT DOCUMENTS

| | | |
|---|---|---|
| 3,424,842 | 1/1969 | Nurnberg . |
| 3,622,677 | 11/1971 | Short et al. . |
| 3,639,169 | 2/1972 | Brong . |
| 4,097,606 | 6/1978 | Chavkin et al. . |
| 4,439,453 | 3/1984 | Vogel . |
| 4,551,177 | 11/1985 | Trubiano et al. .............. 106/210 |
| 4,562,024 | 12/1985 | Rogerson . |
| 4,631,284 | 12/1986 | Salpekar et al. .............. 514/277 |
| 4,820,522 | 4/1989 | Radebaugh et al. . |
| 4,851,230 | 7/1989 | Tencza et al. .............. 424/467 |
| 4,874,757 | 10/1989 | Crawford et al. . |
| 4,894,236 | 1/1990 | Jang et al. . |
| 4,915,953 | 4/1990 | Jordan et al. . |
| 4,968,509 | 11/1990 | Radebaugh et al. . |
| 4,983,399 | 1/1991 | Maish . |
| 5,004,613 | 4/1991 | Radebaugh et al. . |
| 5,037,658 | 8/1991 | Urban et al. . |
| 5,130,140 | 7/1992 | Urban et al. . |
| 5,198,228 | 3/1993 | Urban et al. .............. 424/469 |

OTHER PUBLICATIONS

Falzone et al., Drug Dev Ind Phar 18 (4): 468-489 (1992).

Primary Examiner—Marianne M. Cintins
Assistant Examiner—Keith MacMillan
Attorney, Agent, or Firm—Robert E. Kosinski

[57] ABSTRACT

A direct compression granulated acetaminophen tableting composition is prepared by blending acetaminophen with a binder, disintegrant, lubricant and a small amount of water or alcohol, compacting the blend, preferably by roller compacting into sheets, and milling the compacted product into granulated particles of a desired particle size suitable for direct compression tableting.

10 Claims, No Drawings

METHOD FOR PREPARING A DIRECT COMPRESSION GRANULATED ACETAMINOPHEN COMPOSITION

BACKGROUND OF THE INVENTION

This invention relates to a formulation and method for preparing a granulated acetaminophen composition suitable for direct compression into tablets.

A tablet is a complex dosage form of blends of particulate solid materials comprising active pharmaceutical ingredients. Ease of administration and availability in a variety of shapes and sizes make tablets a universally accepted and most commonly used oral dosage form. Tablets are compressed from blends of particulate solid materials with good flow and compressibility characteristics, which, in many instances, have been pre-granulated to promote compressibility into a tablet. In addition to an active drug, a tablet blend may contain several inactive but essential ingredients, such as binder, bulking agent, disintegrant, flow enhancer, lubricant, etc. In general, the principal methods used by the pharmaceutical industry to prepare tablet blends are:

Direct Compression or Dry Blend—A dry blend suitable for direct compression is prepared by a simple mixing process. This is the preferred method for low dose drugs and for drugs that inherently possess good compression characteristics. Simplicity of the method and resulting advantages of time and resource savings make this a very desirable method for tablet manufacturers.

Wet Granulation—A wet granulation technique requires preparation of a blend, wetting the blend with a large amount of binder solution to a wet mass, milling the wet mass into moist granules agglomerated with a binder and drying the granules, followed by further milling and blending with other inactive ingredients. This is a lengthy and resource intensive process. For drugs that are not compressible and lack required flow characteristics, this process of agglomeration with a binder results in a compressible granulation.

Commercially available direct compression granulations of acetaminophen are prepared by a variety of wet granulation techniques utilizing a variety of inactive tableting ingredients and granulating equipment. A typical granulation is prepared in a conventional granulator, high sheer granulator or fluid bed granulator. Drying of the wet granular mass is usually achieved in a fluid bed dryer.

Dry Granulation—A dry granulation is prepared by compacting a dry powder blend of the drug and inactive tableting ingredients using roller compacting or slugging equipment, milling the compact and blending the resultant granulation with other inactive ingredients. This method is commonly used for blends of drugs that are compressible but do not have required flow characteristics or for drugs that have marginal compressibility, e.g., aspirin. Dry granulation requires less processing equipment and provides advantages of economy and through-put over wet granulation.

Aspirin is a commercial example of a direct compression tablet granulation prepared by the dry granulation technique. A typical granulation is prepared by blending aspirin with inactive tableting ingredients in a blender, compacting the blend using a roller compactor, milling to a desired particle size and reblending.

Tablet manufactures generally purchase direct compression granulations of large dosage drugs, such as aspirin or acetaminophen from suppliers who prepare such granulations by the methods described above. Crystalline aspirin is marginally compressible and hence suitable for compaction using slugging or roller compaction, thereby allowing the use of the dry granulation technique with only 10 percent added inactive tableting ingredients.

In contrast, crystalline acetaminophen is very hard and brittle and lacks any compressibility. Due to its poor compression characteristics, the drug cannot be tableted by the dry granulation technique described above.

The prior art has attempted to circumvent the costly wet granulation process by loading dry powder mixtures of acetaminophen with very high weight percents of inactive ingredients, e.g., 25 weight percent and higher, to achieve sufficient compressibility of the mixture for tablet manufacture, meaning only low dosage levels, e.g., 75 and lower weight percent of acetaminophen in a tablet produced by such methods.

Falzone et al, Drug Der Ind Phar 18(4): 468-489, examined the use of a roller compactor to prepare granulated material containing acetaminophen. The granulation contained 20% Avicel PH 101, 20% hydrous lactose and 60% of acetaminophen. The blends were roller compacted under various compactor parameters to assess their effect on particle size distribution and compressibility of the granulations obtained. The roller compaction resulted in a granulation with the same or smaller particle size than that of the starting material. The tablets obtained were very large ½" and 2" size compacts, prepared by using a research level motorized hydraulic press. The large amount of 40% of inactive ingredients in the blend mean only low dosage levels of acetaminophen are obtained in a tablet prepared by the procedure described by Falzone et al.

U.S. Pat. No. 3,639,169 discloses a compression vehicle component prepared for admixture with active materials with poor compression characteristics to provide a dry powder blend for direct compression into tablets. The compression vehicle itself is prepared by blending an inactive compressible material with other inactive tableting materials, roller compacting the blend into a sheet and then milling the sheet into granular particles to form the compression vehicle. As is evident from Example 13, in the pharmaceutical formulations set out at Column 10, lines 5 to 25, the compression vehicle constitutes the major proportion of the tablet formulation, e.g., 117 parts of the compression vehicle and only 25 parts of the drug.

Dry granulation would be a method of choice over wet granulation if a formulation and method could be discovered which could utilize the dry granulation technique to create direct compression tablet blends containing high dosage levels of acetaminophen. There is a substantial need in the art for a formulation and method to overcome the disadvantages inherent in the wet granulation method and produce a lower cost high quality granulation containing a high analgesic dosage level of acetaminophen capable of being directly compressed into a superior quality tablet.

SUMMARY OF THE INVENTION

Acetaminophen is an analgesic and antipyretic. It is usually marketed in 325 mg and 500 mg tablets of various shapes and sizes. These tablets have a high dosage level of the drug and are large in size. Accordingly, the tablet blend must contain a high weight percentage of acetaminophen, e.g., about 70 to 95, preferably about 90, weight percent. Tablet blends containing such high amounts of acetaminophen, binder and other tableting aids have not been, and cannot be, roller compacted into compressible granulations using the above described dry granulation technique. In accordance with the present invention it has been discovered that incorporating a small amount of water or alcohol along with binder in an acetaminophen blend creates a composition that enables compaction granulation at high levels of drug loading.

The present invention relates to the preparation of a directly compressible granulation of acetaminophen by the dry granulation technique. The formulation and method of the invention delivers granular compositions comprising a high level of acetaminophen for direct compression into tablets. In general, the method comprises blending from about 70 to about 95, preferably about 90, weight percent, of acetaminophen, binder, disintegrant, lubricant, and a small amount of water or alcohol, compacting the blend, milling the compacted material into granulated particles of desired particle size and optionally further blending the granulated particles with lubricant to attain a formulation of desired compressibility and flow characteristics. The granulations afforded by this invention are tabletable over a wide range of pressures providing tablets with acceptable friability and rapid disintegration time. Excellent quality tablets having high dosage levels of acetaminophen are obtained. Furthermore, the tedious and costly process of wet granulation is eliminated.

DETAILED DESCRIPTION

In accordance with the present invention, a formulation and method has been discovered to make granulated particles comprising high dosage levels of acetaminophen suitable for direct tableting. The formulation of the invention comprises acetaminophen, typically from about 70 to about 95, preferably 90, weight percent, binder in an amount from about 1 to about 10 weight percent, a disintegrating agent, typically from about 0 to about 2 weight percent, a lubricant, typically from about 0.5 to about 3 weight percent and water or alcohol in an amount from about 1 to about 7 weight percent.

A formulation according to the foregoing composition is mixed in a blender. The resultant composition is then compacted, preferably by roller compaction into sheets using conventional roller compactors, e.g., a Model L-83 Chilsonator manufactured by the Fitzpatrick Company, Elmhurst, Ill. The compacted material is then milled into granulated particles of a desired particle size, and additional lubricant added, if desired, for proper flow and tableting properties. The resultant product is suitable for direct compression into superior tablets with respect to compressibility, hardness, tablet esthetics and rapid disintegration and dissolution times.

USP grade acetaminophen is used in the formulation and method of the present invention. It is commercially available from several manufacturers.

Suitable binders include starch, modified starch, partially or completely pregelatinized starch, microcrystalline cellulose, e.g., Avicel PH 101, PH 102, PH 103 and PH 200 grades, a homopolymer or a copolymer of vinyl acetate and vinyl pyrollidone (PVP), such as, PVP K-29-32, PVP K-26-28 and PVP K-90, methyl cellulose, hydroxypropyl cellulose and hydroxypropyl alkyl cellulose, e.g., hydroxypropyl methyl cellulose and combinations thereof.

The disintegrant component includes commonly used disintegrants, such as, croscarmellose sodium (Ac-Di-Sol), crosslinked carboxy methyl cellulose, sodium starch glycolate, Povidone XL, starch, partially pregelatinized starch, microcrystalline cellulose, alginic acid and its salts, and combinations thereof. It is added in an amount sufficient to insure that the tablet product manifests an appropriate disintegration time, preferably in the range of from about 0 to about 2 weight percent.

Suitable lubricants include stearic acid, stearate salts, such as calcium, magnesium and zinc stearate, colloidal silica, polyethylene glycol, hydrogenated vegetable oils, colloidal silica, talc, and combinations thereof. The lubricant is present in an amount sufficient to impart the desired lubricity to the granulation, typically in an amount from about 0.5 to about 3 weight percent. Preferred lubricants are stearic acid and colloidal silica. The lubricant may be added in whole or in part to the initial blend and the balance, if any, blended with the granulated particles comprising acetaminophen obtained from the milling step.

Water is present in an amount from about 1 to about 7 weight percent. An alcohol, e.g., methanol, ethanol, isopropanol, etc., alone, or in combination with water, may be used in place of water.

The formulation is typically prepared by initially mixing the acetaminophen, binder, disintegrant, water or alcohol and at least a portion of the lubricant in a conventional pharmaceutical blending apparatus, such as a V-Blender. The resultant blend is fed to a compactor, preferably a roller compactor such as one made by Alexanderwerk or a Chilsonator manufactured by the Fitzpatrick Company, which converts the blend into a compacted sheet. The rate of feed, roller pressure and compaction speed are adjusted to obtain a compact sheet that does not disintegrate under slight pressure or form an undesirable amount of dust upon milling.

The next step of the process of this invention is milling to reduce the compacted material, e.g. compacted sheet obtained by roller compaction, to granulated particles of a desired particle size distribution, which is carried out with conventional milling equipment, e.g., Fitzmill, Oscillator, Comil, etc. The resultant granulated product by itself or optionally blended with lubricant is suitable for direct compression into tablets using conventional tableting machinery, e.g., Manesty Rotary Press. Stokes Rotary Press, etc. at conventional compression pressures.

The following examples illustrate the invention.

EXAMPLE 1

The following formulation was used in this example:

TABLE I

| Ingredient | Weight (%) |
| --- | --- |
| Acetaminophen, USP | 90.0 |
| Pregelatinized Starch, NF (Starch 1500) | 3.5 |
| Povidone, USP (K-90) | 2.0 |
| Croscarmellose Sodium, NF (Ac-Di-Sol) | 2.0 |
| Stearic Acid, NF | 2.0 |
| Colloidal Silicon Dioxide, NF (Syloid 244) | 0.5 |
| Total | 100% |
| Water | 100 ml |

Acetaminophen (4.50 kg), Starch 1500 (0.175 kg), Povidone K-90 (0.100 kg), and half of Ac-Di-Sol (0.050 kg) were mixed in a V-Blender for 5 minutes without an intensifier bar and then for 2 minutes with the bar. 100 ml of water was then added over a 90 second period while mixing with the intensifier bar and mixing was continued for an additional 3 minutes and 30 seconds with the intensifier bar. Half of the Stearic acid (0.050 kg) was screened through a 30# screen into the blender and mixing was continued for an additional 5 minutes.

The resultant composition was then roller compacted using an Alexanderwerk NP 50 N Roller Compactor equipped with 2.50 mm and 1.25 mm screens. A portion of the resultant granular product (3.65 kg) was charged into a V-Blender. The remaining 1 weight percent of Ac-Di-Sol (0.037 kg) and Syloid 244 (0.019 kg) were added to the blender through a 12# screen followed my mixing for 5 minutes without the intensifier bar. The remaining 1 weight percent of stearic acid (0.037 kg) was then screened through a 30# screen into the blender and mixing was continued for an additional 5 minutes without the intensifier bar. A final granular product of comprising about 90% acetaminophen was obtained.

The resultant granular composition was directly compressed into tablets using a Manesty Express Tablet Press with 7/16" standard concave tooling. The resultant tablets had the properties shown in Table II below:

TABLE II

| Tablet Parameters | |
|---|---|
| Weight | 561 mg |
| Thickness | 0.237" |
| Hardness | 13.1 kp |
| Friability | 0.5% |
| Disintegration time (min:sec) | 1:02 |

EXAMPLE 2

The following formulation was used in this example:

TABLE III

| Ingredient | Amount (%) |
|---|---|
| Acetaminophen, USP | 90.0 |
| Pregelatinized Starch, NF (Starch 1500) | 3.5 |
| Povidone, USP (K-29-32) | 2.0 |
| Croscarmellose Sodium, NF (Ac-Di-Sol) | 2.0 |
| Stearic Acid, NF | 2.0 |
| Colloidal Silicon Dioxide, NF (Syloid 244) | 0.5 |
| Total | 100% |
| Water | 375 ml |

Acetaminophen (10.8 kg), Starch 1500 (0.420 kg), Providone K-29-32 (0.240 kg) and Ac-Di-Sol (0.120 kg) were mixed in a V-Blender for 5 minutes without the intensifier bar and then for 2 minutes with the intensifier bar. 375 ml of water was added over a period of 1 minute and 45 seconds and mixing was continued for an additional 3 minutes and 15 seconds with the intensifier bar. Stearic acid (0.120 kg) was then passed through a 30# screen into the blender and mixing was continued without the intensifier bar for 5 minutes. The resultant composition was roller compacted using the apparatus employed in Example 1. A portion of the resultant granular product (4.875 kg) was fed into a V-Blender. A blend of 1 weight percent Ac-Di-Sol (0.050 kg) and 0.5 weight percent Syloid 244 (0.025 kg) was then passed through a 20# screen into the blender and mixing was continued for 5 minutes without the intensifier bar. The remaining stearic acid (0.050 kg) was passed through a 30# screen into the blender and mixing was continued for an additional 5 minutes without the intensifier bar.

The final granular composition comprising acetaminophen was compressed into tablets using 15/32" flat face bevel edge tooling on the Manesty Express Tablet Press. The resultant tablets had the properties shown in Table IV below:

TABLE IV

| Tablet Parameters | |
|---|---|
| Weight | 561.1 mg |
| Thickness | 0.176" |
| Hardness | 11.4 kp |
| Friability | 0.44% |
| Disintegration (min:sec) | 00:55 |

EXAMPLE 3

The following formulation was used in this example:

TABLE V

| Ingredient | Amount (%) |
|---|---|
| Acetaminophen, USP | 90.91 |
| Pregelatinized Starch, NF (Starch 1500) | 3.54 |
| Povidone, USP (K-90) | 2.02 |
| Croscarmellose Sodium (Ac-Di-Sol) | 1.01 |
| Stearic Acid, NF | 2.02 |
| Colloidal Silicon Dioxide (Syloid 244) | 0.50 |
| Total | 100% |
| Water | 1050 ml. |

Acetaminophen (27.0 kg), Starch 1500 (1,050 kg), Povidone K-90 (0.600 kg) and Ac-Di-Sol (0.300 kg) were mixed in a V-Blender for 5 minutes without the intensifier bar and for 2 minutes with the intensifier bar. Water was added over 2 minutes and 30 seconds using the intensifier bar and mixing was continued for an additional 4 minutes and 30 seconds with the intensifier bar and then for an additional 15 minutes without the intensifier bar. Stearic acid (0,300 kg) was screened through a 30# screen into the blender and mixing was continued for an additional 5 minutes without the intensifier bar. The resultant composition was fed into a L-83 Chilsonator made by the Fitzpatrick Company, Elmhurst Ill., without the J-mill attachment. The compacted sheets were milled in a Comitrol Processor (Model 1700) using 2504 rpm impeller speed and 0,040" cutting head.

A portion of the milled granules (3,500 kg) was loaded into a V-Blender. 0.5 weight percent Syloid 244 (0,018 kg) was passed through a 20# screen into the blender and mixed for 10 minutes without the intensifier bar. The remaining stearic acid (0.036 kg) was passed through a 30# screen into the blender and mixing was continued for 5 minutes without the intensifier bar. The milled granules had a desired particle size distribution and exhibited good flow properties and compressibility profile. The granulation was compressed into tablets on a Manesty Express Tablet Press with 15/32" flat face bevel edge punches, which had the following properties:

TABLE VI

| Tablet Parameters | |
|---|---|
| Weight | 555 mg |
| Thickness | 0.177" |

TABLE VI-continued

| Tablet Parameters | |
|---|---|
| Hardness | 9.0 kp |
| Friability | 0.45% |
| Disintegration Time (min:sec) | 00:45 |

EXAMPLE 4

The milled granulation from Example 3 was compressed without further lubrication, using the tablet press and punches described in Example 3. The tablets had the following properties:

TABLE VII

| Tablet Parameters | |
|---|---|
| Weight | 556 mg |
| Thickness | 0.177" |
| Hardness | 9.6 kp |
| Friability | 0.58% |
| Disintegration time (min:sec) | 00:45 |

EXAMPLE 5

The milled and lubricated granulation from Example 3 was compressed on a Manesty Express Tablet Press with 0.230"×0.750" capsule shaped tooling into tablets, which had the following properties:

TABLE VIII

| Tablet Parameters | |
|---|---|
| Weight | 562 mg |
| Thickness | 0.237" |
| Hardness | 9.2 kp |
| Friability | 0.37% |
| Disintegration time (min:sec) | 00:33 |

EXAMPLE 6

The following formulation was used in this example:

TABLE IX

| Ingredient | Amount (%) |
|---|---|
| Acetaminophen, USP | 89.5 |
| Pregelatinized Starch (Starch 1500) | 6.0 |
| Povidone, USP (K-90) | 1.0 |
| Croscarmellose Sodium, NF (Ac-Di-Sol) | 1.0 |
| Stearic Acid, NF | 2.0 |
| Colloidal Silicon Dioxide, NF (Syloid 244) | 0.5 |
| Total | 100% |
| Water | 900 ml |

Acetaminophen (27.0 kg), Starch 1500 (1.800 kg) Povidone K-90 (0.300 kg) and Ac-D-Sol (0.300 kg) were mixed in a V-Blender for 5 minutes without the intensifier bar and then mixed for an additional 2 minutes with the intensifier bar. 900 ml of water was added over 1 minute using the intensifier bar and mixing was continued for 6 minutes with the intensifier bar and then for an additional 15 minutes without the intensifier bar. Stearic acid was passed through a 30# screen into the blender. The resulting blend was fed to the Model L-83 Chilsonator with a J-mill attachment with a 0.093" screen. The granulation obtained had a desired particle size distribution and bulk density. A portion of the granulation obtained was loaded into a V-Blender. A mixture of the remaining stearic acid and Syloid 244 was passed through a 30# screen into the blender and the composition mixed for 5 minutes without the intensifier bar.

The composition obtained was compressed into tablets using a Manesty Express Tablet Press and 15/32" flat face bevel edge tooling. The tablets obtained had the following properties:

TABLE X

| Tablet Parameters | |
|---|---|
| Weight | 550.5 mg |
| Thickness | 0.179" |
| Hardness | 12.1 kp |
| Friability | 0.79% |
| Disintegration (min:sec) | 00:31 |

EXAMPLE 7

The following formulation containing 7 percent of water was used in this example:

TABLE XI

| Ingredient | Amount (%) |
|---|---|
| Acetaminophen | 90.91 |
| Pregelatinized Starch, NF (Starch 1500) | 3.54 |
| Povidone, USP (K-90) | 2.02 |
| Croscarmellose Sodium, NF (Ac-Di-Sol) | 1.01 |
| Stearic Acid | 2.02 |
| Colloidal Silicon Dioxide, NF (Syloid 244) | 0.50 |
| Total | 100% |
| Water | 700 ml |

Acetaminophen (9.00 kg), Starch 1500 (0.350 kg), Povidone K-90 (0.200 kg) and Ac-Di-Sol (0.100 kg) were mixed in a V-Blender for 5 minutes without the intensifier bar and for 2 minutes with the intensifier bar. 700 ml of water was added over 2 minutes using the intensifier bar and mixing was continued for an additional 3 minutes with the intensifier bar and then for an additional 15 minutes without the intensifier bar. Stearic acid (0,100 kg) was screened through a 30# screen into the blender and mixing was continued for an additional 5 minutes.

The resulting composition was fed to the Model L-83 Chilsonator, without the J-mill attachment. The compacted sheets obtained were milled in a Comil milling machine using a type 1601 impeller and 0.083" screen at 2000 rpm. A portion of the milled granules were lubricated with the remaining stearic acid and Syloid 244. 15/32" round tablets were compressed using conventional tablet machinery and displayed the following properties:

TABLE XII

| Tablet Parameters | |
|---|---|
| Weight | 554 mg |
| Thickness | 0.177" |
| Hardness | 8.2 kp |
| Friability | 0.27% |
| Disintegration time (min:sec) | 01:04 |

Example 8

The formulation of Example 7 was repeated using 3.5% isopropyl alcohol in place of water. The granulation obtained was tableted into 15/32" round tablets, which had the following properties:

TABLE XIII

| Tablet Parameters | |
|---|---|
| Weight | 556 mg |
| Thickness | 0.179" |
| Hardness | 8.1 kp |

TABLE XIII-continued

| Tablet Parameters | |
| --- | --- |
| Friability | 0.71 |
| Disintegration time (min:sec) | 00:32 |

EXAMPLE 9

The following formulation was used in this example:

TABLE XIV

| Ingredient | Amount (%) |
| --- | --- |
| Acetaminophen, USP | 90.66 |
| Microcrystalline Cellulose (Avicel PH 101) | 4.55 |
| Povidone, USP (K-90) | 2.02 |
| Croscarmellose Sodium, NF (Ac-Di-Sol) | 0.25 |
| Stearic acid, NF | 2.02 |
| Colloidal Silicon Dioxide, NF (Syloid 244) | 0.50 |
| Total | 100% |
| Water | 350 ml |

Acetaminophen (9.00 kg), Avicel PH 101 (0.450 kg) and Povidone K-90 (0.200 kg) were mixed in a V-Blender and water and stearic acid were therewith according to procedure described in Example 7. The resulting blend was chilsonated using the L-83 Chilsonator without the J-mill attachment. The chilsonated sheets obtained were milled using a Comil milling machine with a type 1601 impeller and 0.094" screen at 2000 rpm. A portion of the milled granulation as mixed with 0.25% Ac-Di-Sol in a V-Blender for 10 minutes followed by mixing with about 1% stearic acid for 5 minutes. The granulation was tableted using a Manesty Express Tablet Press with 15/32" flat face bevel edge tooling. The tablets had the following properties:

TABLE XV

| Tablet Parameters | |
| --- | --- |
| Weight | 564 mg |
| Thickness | 0.172" |
| Hardness | 15.1 kp |
| Friability | 0.49% |
| Disintegration time (min:sec) | 03:14 |

It is to be understood that the embodiments described above are simply illustrative of the principles of the invention. Various other modifications and changes may be made by those skilled in the art which will embody the principles of the invention and fall within the scope thereof.

I claim:

1. A method for preparing a free-flowing particulate granulated acetaminophen composition for direct compression tableting, which comprises:
   (A) blending a mixture of from about 70 to about 95 percent of acetaminophen by dry weight of the blend, from about 1 to about 10 percent of binder by dry weight of the blend, from about 0.5 to about 3 percent of lubricant by dry weight of the blend, from about 0 to about 2 percent of disintegrating agent by dry weight of the blend and from about 1 to about 7 percent of a liquid selected from the group consisting of water, methanol, ethanol, isopropanol and mixtures thereof by dry weight of the blend;
   (B) compacting the blend of Step A to form a compact; and
   (C) milling the compact of Step B to form the said granulated acetaminophen composition.

2. The method of claim 1 wherein a portion of the lubricant of the mixture of Step A is mixed with the granulated acetaminophen of Step C.

3. The method of claim 1 wherein in Step B the blend is roller compacted to form a compact in sheet form.

4. The method of claim 2 wherein in Step B the blend is roller compacted to form a sheet.

5. The method of claim 1 wherein in Step A the acetaminophen is present in an amount of about 90 percent by dry weight of the blend.

6. The method of claim 2 wherein in Step A the acetaminophen is present in an amount of about 90 percent by dry weight of the blend.

7. The method of claim 3 wherein in Step A the acetaminophen is present in an amount of about 90 percent by dry weight of the blend.

8. The method of claim 4 wherein in Step A the acetaminophen is present in an amount of about 90 percent by dry weight of the blend.

9. The method of claim 4 wherein in Step A the binder is selected from the group consisting of starch, modified starch, partially or completely pregelatinized starch, microcrystalline cellulose, a homopolymer or colymer of vinyl pyrollidone and vinyl pyrollidone, methyl cellulose, hydroxyalkyl cellulose, hydroxypropyl alkyl cellulose and mixtures thereof.

10. The method of claim 9 wherein in Step A the lubricant is stearic acid.

* * * * *